United States Patent [19]

Garvey, III et al.

[11] Patent Number: 5,354,306
[45] Date of Patent: * Oct. 11, 1994

[54] SURGICAL CLIP

[76] Inventors: Thomas Q. Garvey, III, 10125 Gary Rd., Potomac, Md. 20854; Kathleen Ruddy, 50 Green Village Rd., Madison, N.J. 07940; Frank V. Gates, 9 Yale Dr., Succasunna, N.J. 07876

[*] Notice: The portion of the term of this patent subsequent to Jun. 15, 2010 has been disclaimed.

[21] Appl. No.: 76,404

[22] Filed: Jun. 14, 1993

Related U.S. Application Data

[63] Continuation-in-part of Ser. No. 843,755, Feb. 28, 1992, Pat. No. 5,219,353.

[51] Int. Cl.$^5$ ............................................ A61B 17/00
[52] U.S. Cl. ................... 606/157; 606/158; 24/563; 24/564
[58] Field of Search ............... 606/103, 120, 157-158; 24/457, 543, 563, 704.1, 564

[56] References Cited

U.S. PATENT DOCUMENTS

| | | | |
|---|---|---|---|
| 2,568,511 | 9/1951 | Ogden | 24/253 |
| 2,598,901 | 6/1952 | Garland | 606/120 |
| 2,626,608 | 1/1953 | Garland | 606/120 |
| 3,463,156 | 8/1969 | McDermott | 606/158 |
| 3,705,586 | 12/1972 | Sarracino | 24/543 |
| 4,976,722 | 12/1990 | Failla | 606/158 |
| 5,062,846 | 11/1991 | Oh et al. | 606/158 |

Primary Examiner—Stephen C. Pellegrino
Assistant Examiner—Gary Jackson
Attorney, Agent, or Firm—Levisohn, Lerner & Berger

[57] ABSTRACT

A surgical clip intended to be used with conventional instruments for applying surgical clips, such as those marketed by the United States Surgical Corporation (U.S. Surgical), is disclosed in which the clip fits within and is operated by the movable jaws in the U.S. Surgical Applier but the clip is constructed so as to provide a circumferential closing of the clip around the duct or vessel. The conventional movement of the jaws of the applier operates with the initially open surgical clip, which under pressure by the parallel movement of the jaws, closes about the duct or vessel being occluded and firmly holds the duct in place by capturing the duct between upper and lower arms of the clip.

11 Claims, 8 Drawing Sheets

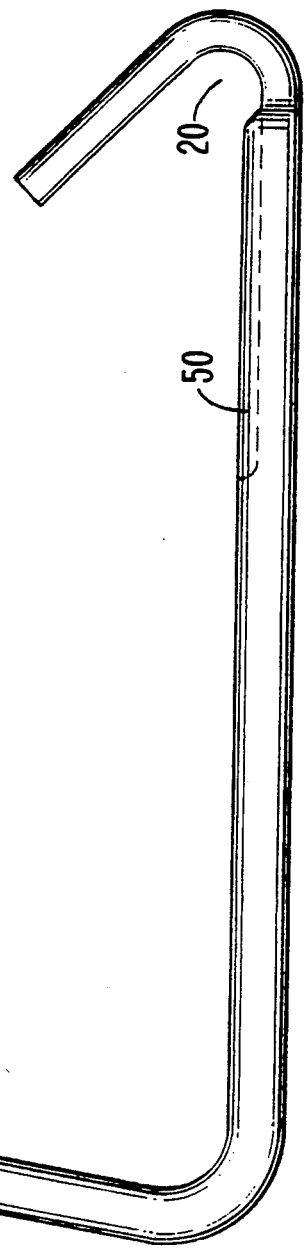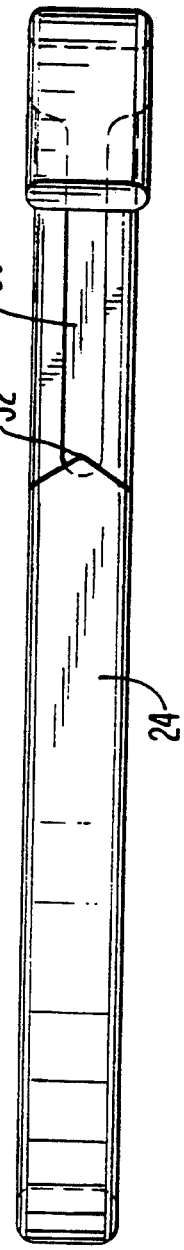
FIG.11
FIG.12

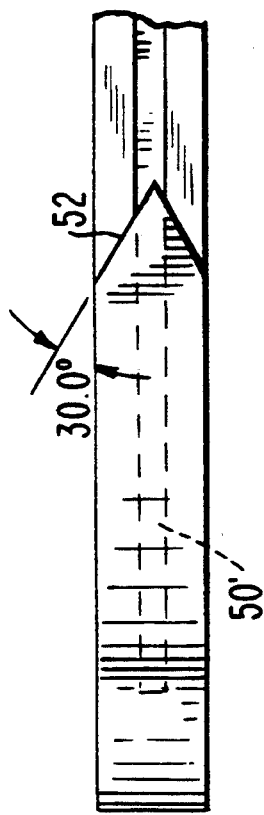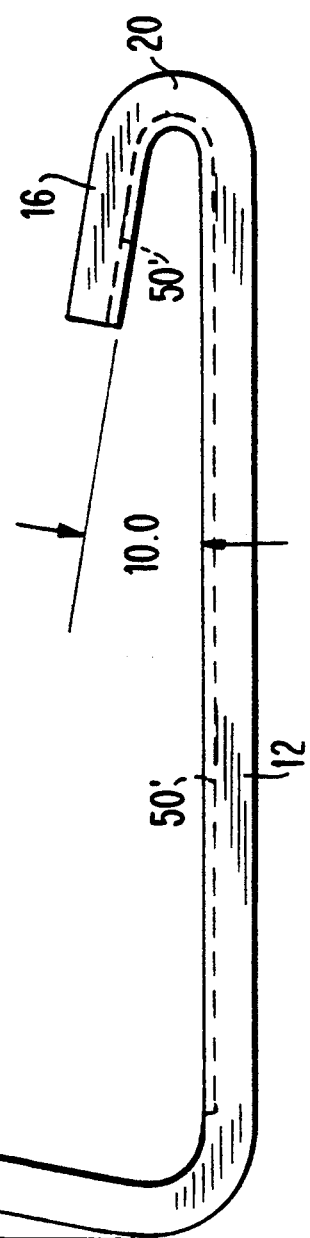
FIG.14
FIG.13

SURGICAL CLIP

RELATED APPLICATIONS

This application is a continuation-in-part of U.S. Pat. Application Ser. No. 07/843,755 filed Feb. 28, 1992, U.S. Pat. No. 5,219,353 to be issued on Jun. 15, 1993.

FIELD OF THE INVENTION

This invention relates to a new and improved surgical clip adapted to be used with either the well known U.S. Surgical Corporation type applier which has achieved widespread use and sometimes is known by the trademark Auto Suture or a modification thereof.

Surgical endoclips are metal devices used to occlude ducts or vessels during surgical procedures. When two clips are applied to a duct or vessel the duct can be severed between them, and if the clips are properly applied and secured, leakage of fluid, such as blood or bile is prevented. Ultimately, the structure occluded by the clip is permanently stenosed and sealed by normal healing processes. The device used to apply an clip can be used for both open and closed, laparoscopic, surgical procedures.

Prior endoclips, made of titanium, are generally U-shaped with the legs squeezed together to seal a vessel. Such clips have a tendency to come off the ducts or vessels to which they have been applied, in part, because the legs may tend to spread apart. Clips have been observed coming off along the transverse axis along which they had been applied as they were being placed and immediately after they had been placed. Such clips also can work themselves off in the severed enid of the duct or vessel along the long axis. In either case, the vessel lumen would cease to be effectively occluded, and bile or blood would be free to leak into in postoperative patients which has sometimes led to surgical re-exploration, transfusion therapy and other untoward complications. Since these problems are not uncommon, the inventors have provided a new clip to reduce the risk of slippage after application.

One of the approved current clips is designed so that the inner surfaces of the U-shaped arms are smooth. Another current clip is designed so that the inner surfaces of its U-shaped arms are corrugated. However, after application, both clips are open and free at one end, even though they are squeezed down across the duct and thus, may slip off the duct along its transverse axis. The occlusions created by and the positions of these clips across the duct are maintained solely by virtue of titanium's lack of "memory"--i.e., once crimped, the clips tend to remain crimped. These clips are not secured in any way other than by squeezing or crimping them across the duct after the clip has been properly placed.

U.S. Surgical Corporation has been very successful in promoting its Auto Suture Disposable Clip Applier. This applier is the subject of several United States Patents, for instance, U.S. Pat. Nos. 4,242,902 and 4,616,650. These patents illustrate that the surgical clips are fed in a cartridge-like fashion between two jaws 103 (FIGS. 14–19 of U.S. Pat. No. 4,616,650), and the patents illustrate the operation of the U.S. Surgical Clip applier and the cartridge fashion in which such clips are supplied.

U.S. Pat. No. 4,834,096 discloses a plastic ligating clip which uses a special manual instrument to close the plastic clip and stop the flow of fluid. The subject of the '096 patent is directed to a plastic clip which, part, is to eliminate metal clips which are objectionable for the reasons set forth in the '096 patent. The '096 clip closes completely around the vessel to which it is secured. The '096 patent presents a special instrument to apply the plastic clip, and the plastic clip is unable to be used with the U.S. Surgical Auto Suture.

There are several other clip tool manufacturers that supply tools that apply clips "manually" i.e., one at a time, "muzzle loaded". This invention is adapted to be used with such surgical clip appliers.

An object of this invention is to provide a surgical clip which may be used with widely accepted types of surgical clip appliers, such that the clips are supplied in a cartridge form to be applied one after another by the surgical clip applier.

Another object of this invention is to provide such a surgical clip which circumferentially surrounds the duct to be closed in a more effective and efficient fashion than prior clips so as to prevent the slippage of such improved clips from the duct.

Still another object of this invention is to provide such an improved surgical clip which will find ready acceptance in the medical field, may be easily utilized with existing technology and provide enhanced benefits.

Another object of this invention is to provide such a surgical clip with nubbins formed on a holding surface thereof to further hold the clip on the duct being occluded when the clip is closed.

Yet another object of the present invention is to positively secure the ends of titanium surgical clips together to ensure the clip's attachment to a vessel.

Still another object of this invention is to provide an improved gripping mechanism to securely hold the ligated vessel and prevent it from slipping.

Another object of this invention is to minimize risk of accidental perforation by any part of the clip.

Other objects, advantages and features of this invention become more apparent from the following description.

SUMMARY OF THE INVENTION

In accordance with the principles of this invention, the above objects are accomplished by providing a metallic clip, which is formed of a thin metallic unitary member generally of an elliptical cross section. The clip has a base which terminates at one end in an upwardly and rearwardly extending section which itself terminates in a lower free-end. The clip also has an upper forwardly extending arm terminating in an upper free-end which is spaced rearwardly from said lower free-end. The base and upper arm are connected by an upwardly extending section bent forwardly toward the free-ends of the clip. When parallel jaws exert inwardly directed parallel forces against the base and upper arm, the upper arm is displaced downwardly toward the base, and the upper free-end moves downwardly until it contacts the base. As the parallel jaw pressure continues to be exerted on the upper arm and base the upper free-end moves forwardly until it is captured by the bend formed by the rearwardly extending section and is trapped there as the upper arm and lower base move together to circumferentially surround the vessel. The positive lock formed by the rearwardly extending section bearing against the upper free-end ensures that the surgical clip can not open while in place on the vessel.

As a further feature of this invention, a nubbin is provided upon the inner surface of the base in order to further ensure the attachment of the clip to the vessel, and the nubbin may also be shaped to puncture the vessel as the clip is applied to the vessel. As still a further feature of this invention, the free end of the upper arm cooperates with a grove formed in the upper surface of the base to fit therewithin and be prevented from lateral movement as the clip is closed.

A further feature of this invention is realized by providing a groove or slot across the entire upper portion of the lower arm which further holds the vessel or duct in place by squeezing a portion thereof into the groove when the endoclip is closed.

As a further feature, the tail is initially set at a ten degree (10°) angle to reduce the possibility of accidental puncture. This angle is less than previously identified and has been provided to minimize possible snagging yet provide sufficient clearance for the clip to be closed in the manner taught.

BRIEF DESCRIPTION OF THE DRAWING

FIG. 11 is an end view of another embodiment of this invention with features that limit lateral movement of the mating clip motions;

FIG. 12 is a top view of the embodiment of FIG. 11;

FIG. 13 is a side view of another embodiment of the surgical clip of the invention;

FIG. 14 is a partial top view of the clip of FIG. 13

DETAILED DESCRIPTION

Figure 1:
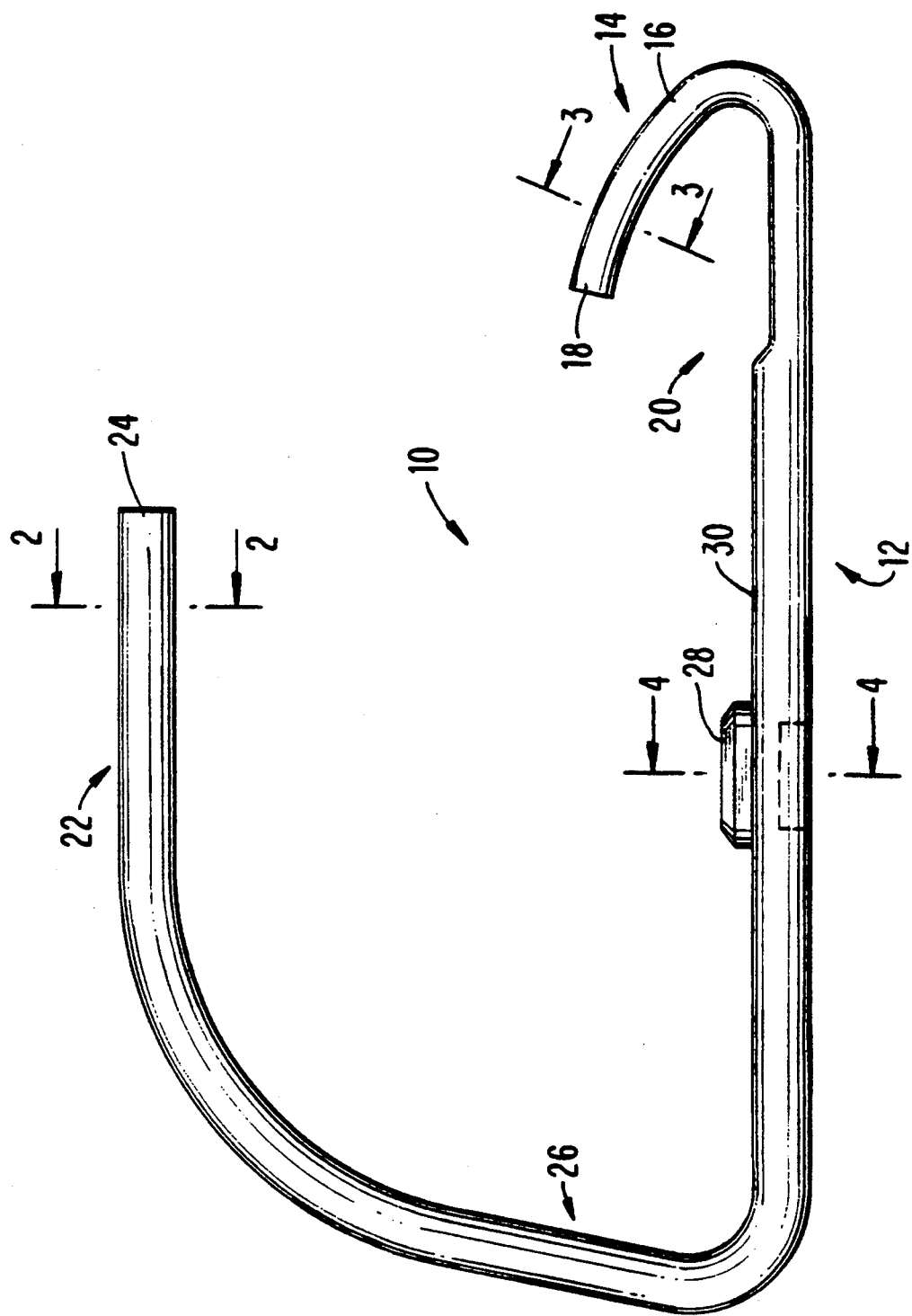
FIG. 1 is an end view of an embodiment of the surgical clip of this invention.

FIG. 1 is an end view of the clip of this invention, generally designated with numeral 10. The clip is formed of a thin metallic unitary member generally of an elliptical cross section. Because of its bio-compatability, Titanium is the preferred metal. The clip 10 has a lower straight base or lower arm 12 which terminates at one end 14 in an upwardly and rearwardly extending tail section 16, which itself terminates in a lower free-end 18. A corner or knee 20 is formed where tail section 16 turns rearwardly. The clip 10 has an upper forwardly extending arm 22 terminating in an upper free-end or tip 24 which is spaced rearwardly from said tail 16. The lower arm 12 and upper arm 22 are connected by an upwardly and forwardly elbow section 26. A nubbin 28 is formed on the upper surface 30 of lower arm or base 12.

Figure 2:
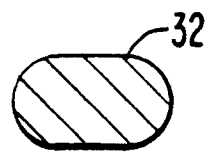
FIG. 2 is a sectional taken along lines 2—2 of FIG. 1.
Figure 3:
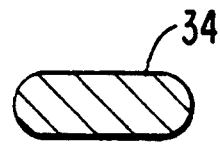
FIG. 3 is a sectional taken along lines 3—3 of FIG. 1.
Figure 5:
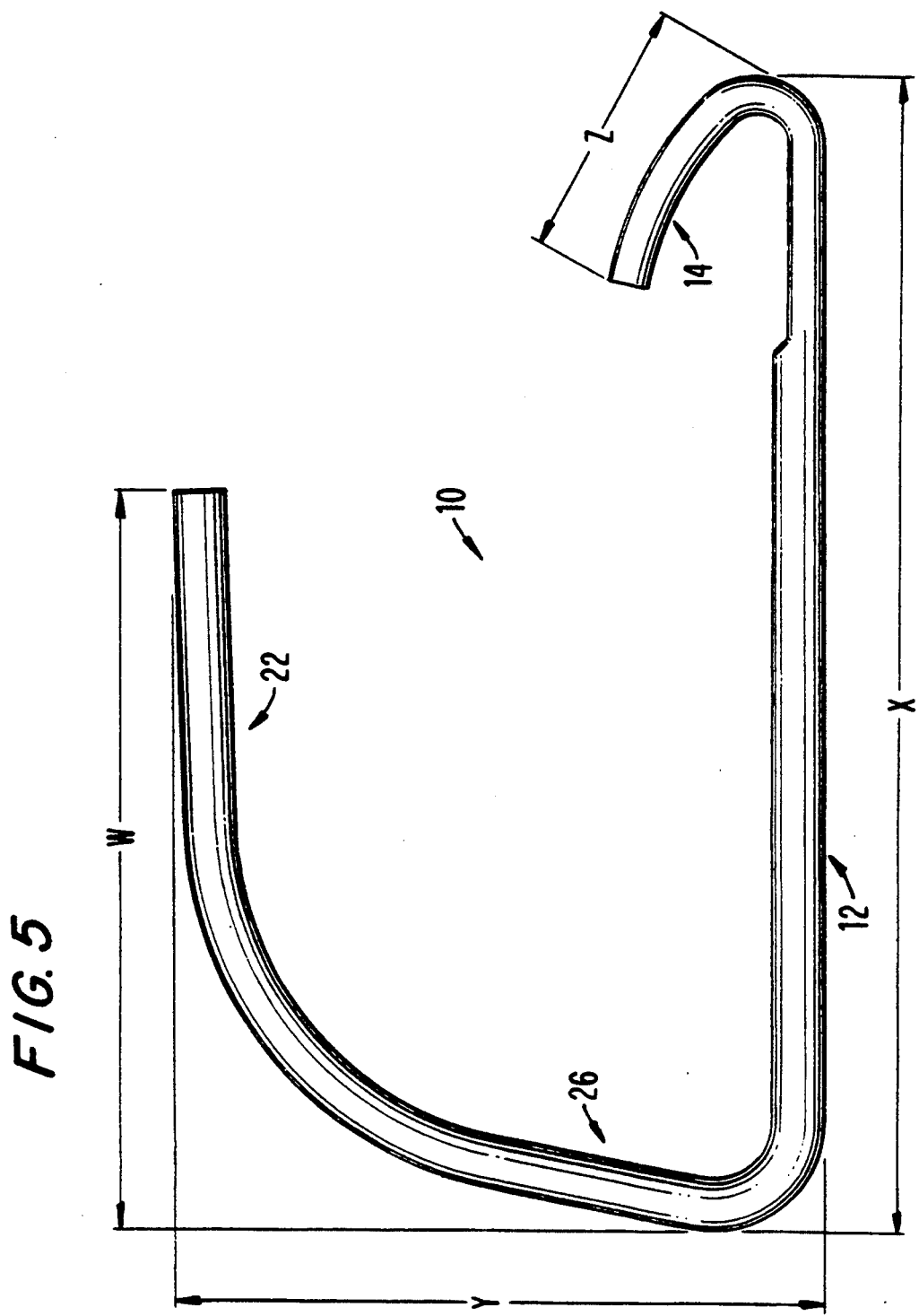
FIG. 5 is an alternate embodiment of the surgical clip of this invention without a nubbin with the clip shown in its open initial position.
Figure 6:
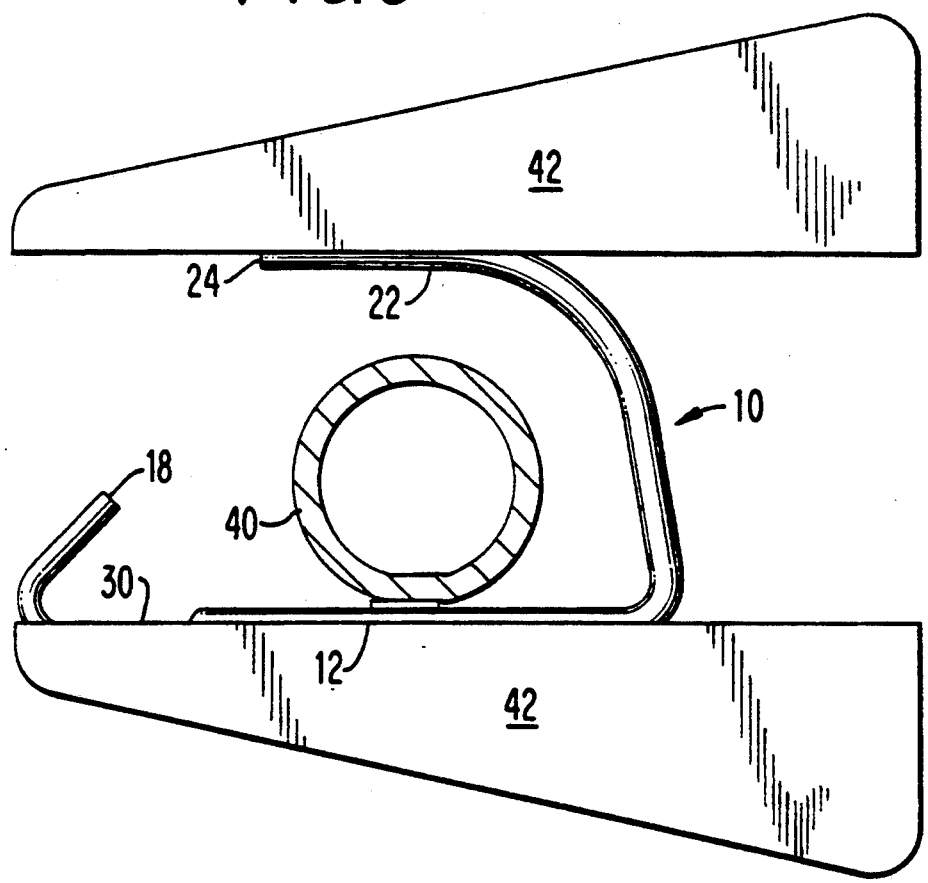
FIGS. 6–10 illustrate the surgical clip of this invention as it is closed and applied to the vessel.
Figure 7:
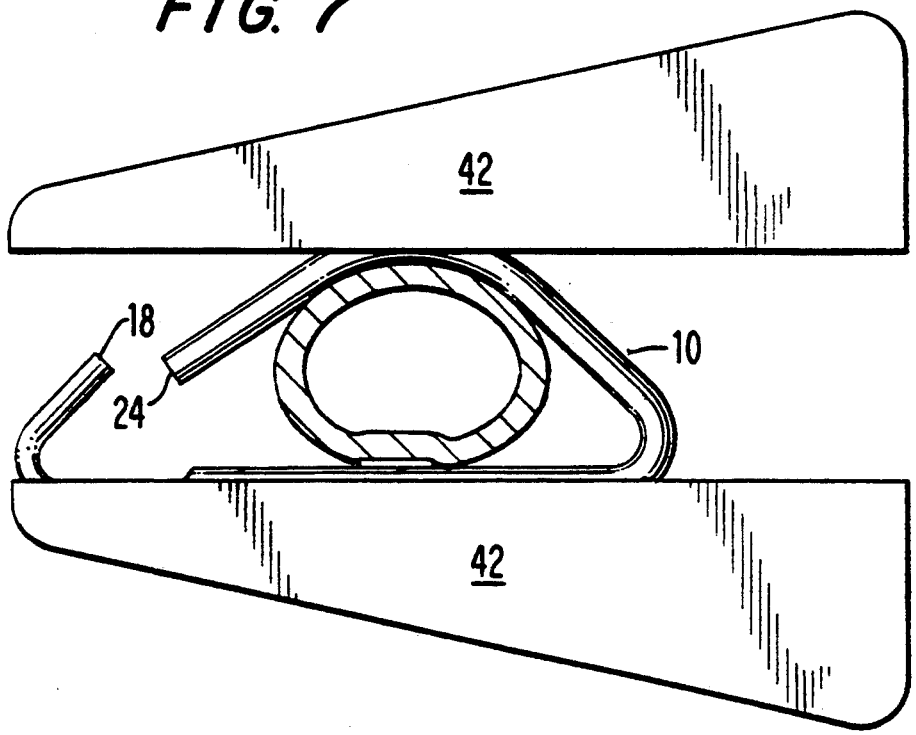
Figure 8:
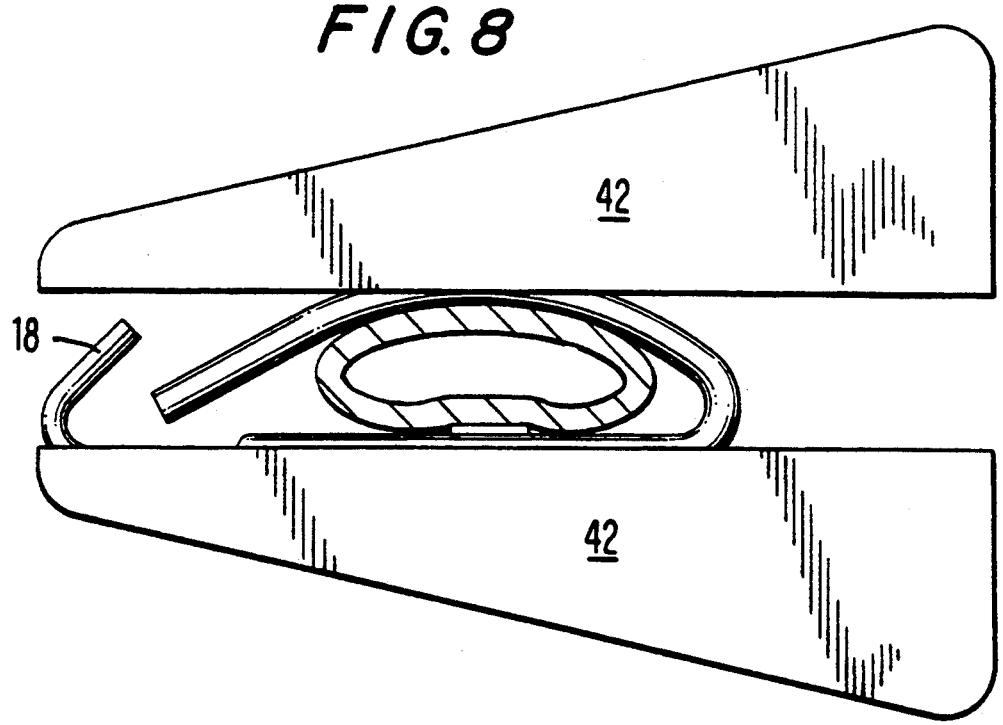
Figure 9:
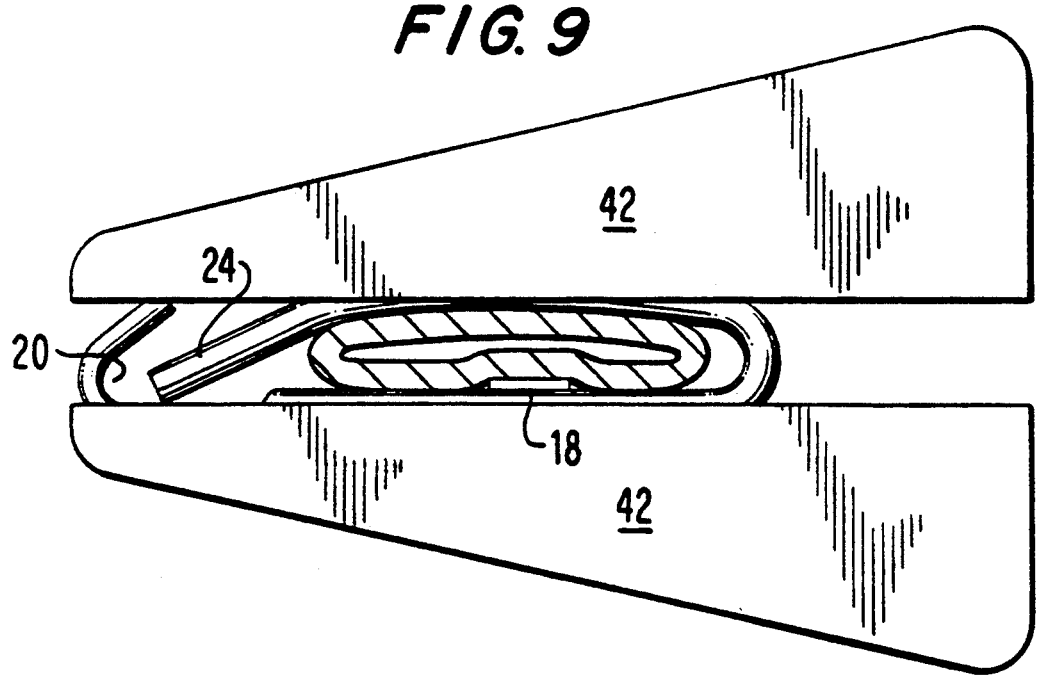

Specific angles and radii are shown in FIG. 1 for the clip. FIG. 5 shows the same clip having the same form, radii and angles as depicted in FIG. 1, but without the nubbin. Sectional views 2, 3 and 4 taken along lines 2—2, 3—3 and 4—4 illustrate the preferred shapes of the cross-sections of the specific section identified of the clip. In particular, the clip 10 has substantially uniform elliptical cross section 32 illustrated in FIG. 2—2 which is formed for most of the clip, with the forward end 34 of the base 12, the corner 20 and rearwardly extending section 16 having a smaller elliptical cross section as illustrated in FIG. 3. This enables the corner or knee portion of the clip when fully closed to have a substantially uniform cross section, since the thickness of corner portion is smaller than the cross section for the remaining portion of the clip as illustrated in FIG. 2.

Figure 4:
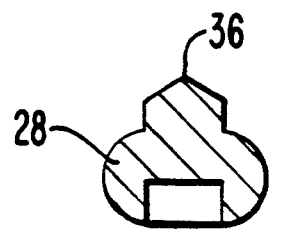
FIG. 4 is a sectional taken along lines 4—4 of FIG. 1.

As illustrated in FIG. 4, the nubbin 28 is provided with a pointed upper surface 36 adapted to pierce the vessel to which the clip is attached to further secure the clip to the vessel.

As described, this invention is intended to be used with a device similar to that of the Auto Suture sold by U.S. Surgical. As described in U.S. Pat. No. 4,616,650, jaws 103 move in parallel planes towards each other, and such Auto Suture or a modified version thereof is intended to be used with the clip of this invention.

FIG. 5 is a view of the clip of this invention without nubbin 28. The same numerals apply for the same parts, and the radii and angles are the same as for FIG. 1.

Although the clip will work at any scale, the preferred embodiment of some important proportionalities as illustrated in FIG. 5 are:

$$\frac{Z}{X} = .222$$

$$\frac{Y}{X} = .614$$

$$\frac{W}{X} = .558$$

With these ratios, the clip is unlikely to effectively work if:

| W increases by approximately 5% |
| :---: |
| or |
| decreases by approximately 10% |

Figure 10:
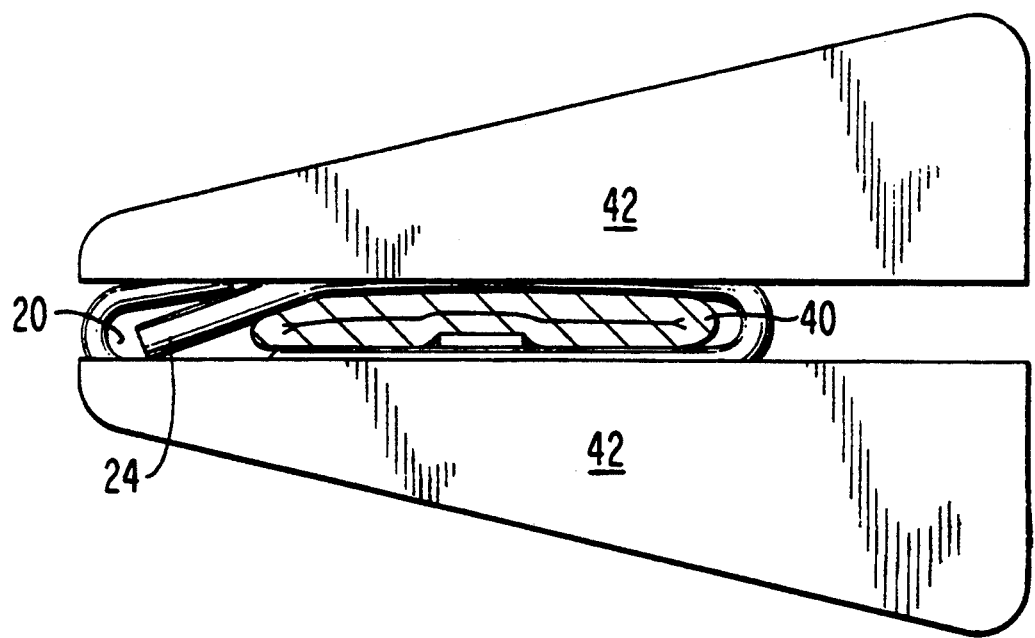

FIGS. 6–10 illustrate the clip in successive stages of deformation as it is applied to occlude a vessel 40. When the parallel jaws 41–42 exert inwardly directed forces against the lower arm 12 and upper arm 22, the upper arm is displaced downwardly toward the lower arm, and the upper free-end 24 moves downwardly until it abuts the inner surface 30 of the base 12. As the jaw forces continue to be exerted on the upper arm 12 and lower arm 10, the tip 24 moves outwardly until it is captured under the tail 16 into knee or corner 20 and is trapped there. As the upper arm 22 and lower arm 12 move further together to circumferentially surround the vessel, the upper free-end 24 is locked into the corner 20 and is positively held there by lower free-end 18. Further inward motion of the jaws causes contact between the upper jaw and free end 18. The free end then collapses, pinching the tip 24 between lower arm 14 and tail 16. This positive lock ensures that the surgical clip circumferentially surrounds the vessel and will not open while in place on the vessel. Nubbin 18 further insures that the clip. 10 will stay in place on the vessel. FIG. 10 illustrates the final shape of the deformed clip 10 gripping the duct or vessel 40.

The new clip 10 of this invention would initially be placed across the transverse axis of the duct 40, and it will be squeezed down in such a way that the clip 10 will end up surrounding and squeezing the duct while the ends of the clip are held together. The inward nubbin 18 on one or both arms of the clip 10 provide significant resistance to movement of the clip along the long axis of the duct.

FIGS. 11 and 12 present yet another embodiment of this invention in which lateral movement between tip 24 and the lower arm 12 is restrained by forming a groove or slot 50 in upper portion 30 of the lower arm 12 and a Vee 52 on the tip end 24 so that Vee 52 fits into groove 50 as the upper arm 22 moves downward and is captured in the corner 20. Lateral movement between the ends of the clip is thus restrained and the upper arm 22 is aligned with lower arm 12 further ensuring the circumferential secure closing of the clip.

In summary, the new clip 10 would incorporate three novel elements:
1. One or two "nubbins" or a ridge, on the inner surface in contact with the vessel or ducts of one or both arms of the clip which, after application of the clip, would substantially increase resistance to slippage in both parallel and orthogonal directions with respect to the long axis of the occluded vessel or duct;
2. Complete, circumferential contact of the clip with the duct or vessel; and
3. Fixation of the ends of the clip together in such a way as to reduce greatly dependence on titanium's lack of "memory" or springiness for maintenance of the vessel or duct closure.

FIGS. 13 and 14 refer to yet another embodiment of this invention. It has been discovered that slot 50 identified in FIG. 11 serves as an aid to capture the occluded vessel when the clip is closed. In order to enhance such capture facility, FIG. 13 shows an end view of the additional embodiment of this invention in which the slot 50 is shown extended across the full width of lower arm 12 with slot 50 being designated as 50' in FIG. 13. Slot 50' is also extended around the knee and to the terminus of tail portion 16 so as to provide an additional recess groove or slot area in which the occluded vessel can be captured. Additionally, tail 16 is initially set to be at approximately ten degrees (10°) with respect to lower arm 12. Note that the angle of tail 16 in FIG. 1 is shown to be 35°. It has been discovered that additional safety enhancements are provided by lowering the above-identified angle so as to minimize accidental puncture of the vessel or duct. The operation of the surgical clip of FIGS. 13 and 14 is substantially identical to that described with respect to FIGS. 6–10.

One of the important advantages of the embodiment of FIGS. 13 and 14 relates to elimination of the nubbin 28 by provision of the extended slot 50' which further helps to secure the vessel or duct against accidental dislodgement after the clip is secured around the vessel or duct.

The angle forming tip 52 is set to be somewhat less than that shown in FIG. 13, and the smaller angle illustrated in FIG. 14 further assists in the tip sliding under the tail 16 engaging in slot 50' formed in that portion of tail 16 which engages with tip 52 as tip 52 slides beneath and is captured in corner or knee 20.

This invention has been described in its preferred embodiment, but modifications therefrom may be made by those of ordinary skill in the art which would still come within the scope and teachings of this invention as set forth in the appended claims.

What is claimed is:

1. A surgical clip comprising a thin metallic unitary member comprising a lower arm terminating in a forward end in an upwardly and rearwardly extending tail section, said upwardly and rearwardly extending tail section terminating in a lower free-end, a corner formed between said tail and said forward end of said lower arm, said clip further comprising an upwardly and forwardly extending intermediate elbow section extending from the rearward end of said lower arm, said upwardly and forwardly extending intermediate elbow section terminating in an upper arm, said upper arm terminating in a forwardly extending tip, said surgical clip having an open position with said upper and lower arms being coplanar, said surgical clip deformable to a closed position by pressure applied to said upper arm and lower arm to move said tip to be captured in said corner under said tail section to form a circumferential closure on a duct to be sealed by said clip, said tip and the upper surface of said lower arm having engaging surfaces along the direction of relative movement between them as said tip moves to be captured in said corner, said tip being moved into and along said interlocking surface of said lower arm as said clip is being closed and the tip is moving forwardly toward said corner, said engaging surfaces guiding the proper closure to maintain the ends within said initial plane as said clip is being closed and preventing said tip and the end of said tail from projecting out from the closed clip to prevent piercing of surrounding tissue, said engaging surface on said lower arm comprising means formed along the upper portion thereof extending across substantially the entire width of the lower arm to hold said vessel.

2. A surgical clip according to claim 1, wherein said tail is initially set at no more than a fifteen degree (15°) angle with respect to the lower arm.

3. A surgical clip according to claim 1, wherein said means is formed in said upper portion and comprises a slot.

4. A surgical clip according to claim 3, wherein said tail is initially set at no more than a fifteen degree (15°) angle with respect to the lower arm.

5. A surgical clip according to claim 3, wherein the tail is initially set at about ten degrees (10°) with respect to said lower arm.

6. A surgical clip as set forth in claim 5, wherein said upper and lower arms are substantially parallel.

7. A surgical clip as set forth in claim 2, wherein said upper and lower arms are substantially parallel.

8. A surgical clip as set forth in claim 1, wherein said metallic member comprises a bio-compatible metal.

9. A surgical clip as set forth in claim 8, wherein said metal is titanium.

10. A surgical clip as set forth in claim 8, wherein the interlocking surface of said upper tip comprises a Vee and the interlocking surface of said lower arm comprises a slot to receive and hold said Vee as said clip is closed.

11. A surgical clip as set forth in claim 2, wherein said upper and lower arms are substantially parallel.

* * * * *